(12) United States Patent
Pasquali et al.

(10) Patent No.: US 8,042,399 B2
(45) Date of Patent: Oct. 25, 2011

(54) METHOD AND A DEVICE FOR INSPECTING A PIPE CONNECTION WELD BY AN ULTRASOUND PROBE

(75) Inventors: Lorenzo Pasquali, Alagna (IT); Massimiliano Rossi, Codogno (IT)

(73) Assignee: Saipem S.A., Montigny le Bretonneaux (FR)

( * ) Notice: Subject to any disclaimer, the term of this patent is extended or adjusted under 35 U.S.C. 154(b) by 832 days.

(21) Appl. No.: 11/988,246

(22) PCT Filed: Jul. 4, 2006

(86) PCT No.: PCT/FR2006/001584
§ 371 (c)(1),
(2), (4) Date: Jan. 3, 2008

(87) PCT Pub. No.: WO2007/006904
PCT Pub. Date: Jan. 18, 2007

(65) Prior Publication Data
US 2009/0078742 A1 Mar. 26, 2009

(30) Foreign Application Priority Data

Jul. 5, 2005 (FR) .................................. 05 07155

(51) Int. Cl.
*G01N 29/26* (2006.01)
*G01N 29/06* (2006.01)
(52) U.S. Cl. ......................................... 73/623; 73/622
(58) Field of Classification Search ............ 73/622–623
See application file for complete search history.

(56) References Cited

U.S. PATENT DOCUMENTS
5,454,267 A 10/1995 Moreau et al.
(Continued)

FOREIGN PATENT DOCUMENTS
FR 2 786 713 9/2000
(Continued)

OTHER PUBLICATIONS

EPO Communication of Allowance dated Mar. 30, 2010.
PCT/FR2006/001584 Written Opinion, Jul. 10, 2008, Saipem S.A. etc.

*Primary Examiner* — Jared Fureman
*Assistant Examiner* — Rose M Miller
(74) *Attorney, Agent, or Firm* — Cozen O'Connor (57) ABSTRACT

A method of inspecting a substantially circular circumferential weld for connecting together an inner pipe and a coaxial outer pipe, either directly or via a junction forging, by using an ultrasound probe having a plurality of robotic multibeam piezoelectric emitter-receivers. The method is performed by: a) positioning at least one ultrasound probe inside said inner pipe; b) scanning the various ultrasound beams from the various emitters of said probe while the probe is positioned at a given position; and c) moving said probe in rotation about the axis of said pipe through a given angle corresponding to an arc length less than or equal to the size of the weld defects that are to be detected; and then d) repeating steps b) and c) until the entire circumference of the weld has been inspected. The present invention also provides a device for inspecting a circumferential weld that is suitable for use in a method of the invention.

19 Claims, 5 Drawing Sheets

U.S. PATENT DOCUMENTS

| | | | |
|---|---|---|---|
| 5,677,490 A * | 10/1997 | Gunther et al. | 73/622 |
| 5,770,800 A | 6/1998 | Jenkins et al. | |
| 6,446,321 B1 | 9/2002 | Marchal | |
| 6,886,407 B1 * | 5/2005 | Fredenberg | 73/622 |
| 7,412,890 B1 * | 8/2008 | Johnson et al. | 73/618 |
| 2003/0136195 A1 | 7/2003 | Krieg et al. | |
| 2004/0118210 A1 * | 6/2004 | Tooma et al. | 73/625 |

FOREIGN PATENT DOCUMENTS

| | | |
|---|---|---|
| GB | 2 161 565 A | 1/1986 |
| GB | 2 191 842 A | 12/1987 |
| WO | WO 01/71338 A | 9/2001 |

* cited by examiner

METHOD AND A DEVICE FOR INSPECTING A PIPE CONNECTION WELD BY AN ULTRASOUND PROBE

PRIORITY CLAIM

This is a U.S. national stage of application No. PCT/FR2006/001584, filed on 4 Jul. 2006. Priority is claimed on the following application(s): Country: France, Application No.: 05/07155, Filed: 5 Jul. 2005; the contents of which is incorporated here by reference.

The present invention relates to a method of inspecting a substantially circular weld for connecting an inner pipe to a coaxial outer pipe, either directly or else via a junction forging, the inspection being performed by means of a probe comprising multibeam ultrasound piezoelectric emitter-receivers.

The present invention also provides a device for inspecting a circumferential weld and suitable for use in a method of the invention.

BACKGROUND OF THE INVENTION

The present invention relates more particularly to the field of double-walled pipes that include an insulating complex, in particular undersea pipes used for conveying hot or cold fluids, and still more particularly pipes constituted by sets of two coaxial pipes of the pipe-in-pipe (PIP) type that comprise an inner pipe and a coaxial outer pipe with an annular space between them, which space preferably contains thermally insulating material.

The present invention relates in particular to undersea pipes with reinforced insulation, of the kind installed on oil fields at great depths, and also to pipes that are suspended between the sea bottom and a surface ship anchored over said oil field.

More precisely, the present invention relates to a method and a device for inspecting welds at the ends of strings of double-walled pipes at the connections between each inner pipe and outer casing.

In most fields of industry, it is desirable to have high-performance insulation systems so as to maintain fluids being conveyed in pipework at constant temperature, so that transfers can be made possible between pieces of equipment over long distances, e.g. as long as several hundreds of meters or even several kilometers. Such distances are commonplace in industries such as oil refineries, liquefied natural gas installations (approximately −165° C.), and off-shore oil fields extending over several tens of kilometers. Such oil fields are being developed in ever-increasing depths of water, which depths can be considerably greater than 3000 meters (m).

Numerous systems have been developed for achieving a high degree of thermal performance, and specific versions have been developed for providing better satisfaction for great depths, i.e. to be capable of withstanding the pressure at the bottom of the sea. The technologies presenting the best performance that have been developed for achieving this object are the so-called pipe-in-pipe technologies in which an inner pipe conveys the fluid and an outer pipe coaxial thereabout comes into contact with the ambient medium, i.e. the water. The annular space between the two pipes can be filled with an insulating material or it can be evacuated of all gas.

In pipes of this type, the annular space optionally filled with insulating material is generally at an absolute pressure that is less than atmospheric pressure, or else is evacuated of all gas, and to a first approximation it can be considered that the inner pipe provides the radial strength for withstanding the bursting pressure due to the internal fluid, while the outer casing withstands implosion due to the hydrostatic pressure at the depth of the bottom (ρ.g.h.) which is about 1 megapascal (MPa) per 100 m depth of water, i.e. MPa for a depth of 3000 m. The axial effect due to pressure, known as the bottom effect, acts on the circular section of the pipe, parallel to the axis of said pipe, and is distributed, to a first approximation, over both of the pipes (since they are connected together at their ends), prorata the respective sections of their material, generally constituted by steel.

For installations at great depths, undersea pipes and undersea sets of coaxial pipes are assembled on land to form unit pipe elements or strings each presenting a unit length lying in the range 20 m to 100 m depending on the size that can be handled by the laying system. They are then transported in this configuration out to sea on board a laying ship. During laying, the unit lengths of the various coaxial pipe assembly elements are connected to one another on board the ship, progressively while they are being laid at sea. It is thus important for the making of such connections to be an integral part of the process of mounting and assembling the pipe and of laying it on the sea bed, while delaying the process as little as possible, so it must be possible to make a connection both quickly and easily.

Patent FR 2 786 713 describes a method of making a connection at each of the ends of a string between an inner pipe and an outer pipe, the end of said outer pipe being set back from the end of said inner pipe, and being deformed by being "crooked" so that its inside diameter at its end is reduced substantially down to the outside diameter of said inner pipe, thus making it possible to make a circular weld connecting together the end of said outer pipe and said inner pipe.

Such internal welds cannot be inspected in conventional manner using X-rays or gamma rays since it is not possible to position a sensitive film circularly around the outside of the inner pipe so that it is centered on the welding bead and covers a certain width on either side of said welding, since the outer casing obstructs access to the zone situated between said outer casing and said inner pipe.

Devices are known for inspecting welding by an ultrasound probe. Such devices are generally operated manually by an operator and they are moved over and close to the weld, both axially in front-to-rear translation over the weld zone, and all around the circumference of the periphery of the pipe in said weld zone, as described in WO 01/71338.

Those devices are constituted by a piezoelectric emitter of ceramic material that emits an ultrasound wave for a short instance, which wave is then coupled into the mass of steel and the metal of the pipe and the weld, and becomes reflected on the opposite surface of the pipe. In general, said emitter also acts as a receiver sensor, with the wave corresponding to the received wave being delivered by electronic processor means to a computer.

Ultrasound probes are also known that comprise a series of emitter-receivers and that are referred to as "phased-array" or multibeam probes. The structure and the operation thereof is explained below, and in particular how to improve inspecting welds, it being possible for the various emitters to emit waves in a common plane perpendicular to the plane of the bottom face of the probe, but in various directions relative to said plane, thus making it possible to extend the geographical zone that is inspected when the probe is positioned in stationary manner, as explained below.

With that type of ultrasound device for inspecting welds, inspection can be performed correctly from the outside on one side only of the weld, towards the end of the string, with the other side of the weld in the space between the pipes remaining inaccessible because of the presence of said outer casing. However, it is possible to inspect the weld in part from the outer casing, except at the root of said weld, where the acoustic echo from the edge cannot be distinguished from a possible welding defect such as a crack initiation site.

Furthermore, by working from the inside, an operator has great difficulty in achieving accurate manual positioning of the ultrasound probe, not only because of the distance between the weld zone for inspection and the end of the pipe, but also because of the difficulty in accurately visualizing the exact position of the weld to be inspected, thus making it very difficult to show up critical welding defects. The problem is made worse when the diameter of the inner pipe is small. Furthermore, when the operator identifies a defect, the exact position of said defect is not known with great precision, specifically because the operation is performed manually.

While laying a PIP, the bending generated creates high levels of stress in the pipe, in particular in the connection zone between two successive lengths of PIP. That is why junction or coupling forgings of steel are often used that are assembled to the ends of the unit elements of sets of coaxial pipes for assembling together. The junction forging at the downstream end of a first unit element of a set of coaxial pipes that are not yet assembled together is connected to the junction forging at the upstream free end of a second set of coaxial pipes that have already been assembled together downstream.

Patents GB 2 161 565 and GB 2 191 842 describe a PIP and a method of assembling it, and also two embodiments of junction forgings or coupling forgings.

In the various embodiments, the junction forging generally includes two tubular branches comprising an outer branch and an inner branch defining an annular space between them, i.e. forming a fork with free cylindrical ends that are assembled to the substantially cylindrical ends respectively of the outer and inner pipes of said PIP type, assembly being performed by welding. The welding zones are then particularly sensitive to the phenomenon of fatigue, both during laying, and throughout the lifetime of the pipe, which is why it is important to be able to inspect the reliability of the welding.

Thus, the problem posed by the present invention is to facilitate and improve performing inspections on welds with the help of an ultrasound probe at the connection between an inner pipe and an outer pipe in a PIP pipe assembly, either when they are directly welded together, or else when they are welded together via forgings.

SUMMARY OF THE INVENTION

To this end, the present invention provides a method of inspecting substantially circular circumferential welding for connecting an inner pipe to a coaxial outer pipe, either directly or else via a junction forging, inspection being performed by an ultrasound probe, and the method characterized by:
using an ultrasound probe comprising a plurality of robotic multibeam piezoelectric emitter-receivers; and
a) positioning at least one said ultrasound probe inside said inner pipe, in the axial direction XX' of said inner pipe against the inside surface of the wall of said inner pipe, facing or close to said weld, so that the ultrasound beams from the various emitters in the axial plane of said inner pipe perpendicular to the plane of the bottom faces of said emitters covers at least the entire width of the weld in said axial direction XX'; and b) causing the various ultrasound beams of the various emitters of said probe to scan while the probe is positioned in a said given position; and
c) moving said probe in rotation about the axis XX' of said pipe through a given angle, preferably less than 1°, more preferably corresponding to an arc of length that is less than or equal to the size of the weld defects that are to be detected; and then
d) repeating steps b) and c) until the entire circumference of said weld has been inspected.

The term "robotic" is used herein to mean that said probe is controlled in operation and in its movements in steps a) do d) by electronic means and a computer.

Advantageously, the ultrasound beams from the various emitters are sent in said axial plane of the inner pipe in a plurality of different angles of inclination ($\alpha$) having different values relative to the plane of said bottom faces of said emitters so that in a single sequence of scanning the various beams, the various zones of said weld are inspected across its width, preferably from the external tip to the root of said weld at the interface with said inner pipe.

In a particular embodiment, said emitters are arranged in three contiguous zones in the axial direction XX', comprising:
a first zone in which the emitters are offset in said axial direction XX' relative to said weld, and emit beams at said angle of inclination towards said weld; and
a central second zone preferably extending over the entire width of said weld and in register with at least the middle portion of the width of said weld, and in which said emitters emit beams substantially perpendicular to the plane of said bottom faces of said emitters; and
a third zone at the end of said central second zone opposite from the end at which said first zone is located, and likewise offset in said axial direction XX' relative to said weld and emitting beams at said angle of inclination towards said weld.

More particularly still, in a first variant:
the various beams of said first zone extend in parallel at a said angle of inclination lying in the range 30° to 60°; and
the various beams of said third zone extend parallel at a said angle of inclination symmetrical to that of the first zone with an opposite angle lying in the range 30° to 60°.

In a second variant, the angles of inclination of the various beams of said first and second zones increase, preferably from 30° to 60° from the emitter that is furthest away from the center of the weld to the emitter that is closest thereto.

In known manner, each said emitter-receiver zone comprises 16 to 1024 piezoelectric elements.

In a first implementation, said weld is made from outside said inner pipe.

In this implementation, and still more particularly, said weld connects the end of an outer pipe to the outside surface of the wall of an inner pipe, the end of said outer pipe being set back from the end of said inner pipe.

In another implementation, said weld is made from the inside of said inner pipe.

In the various ways of performing welding, from the outside or the inside of said inner pipe, said weld may connect the end of said inner pipe to the end of a junction forging.

Still more particularly, said weld is made from the inside of said inner pipe and presents extra thickness relative to the inside surface of the wall of said inner pipe, and two of said ultrasound probes are used placed against said inside surface on either side of said weld, each of said probes comprising a plurality of emitters emitting beams towards said weld, preferably at an angle lying in the range 30° to 60°.

The present invention also provides a device for inspecting a circumferential weld and usable in a method of the invention, the device comprising:

at least one said robotic ultrasound probe comprising a plurality of multibeam piezoelectric emitter-receivers; and mechanical support means for supporting said probe in position against the inside surface of the wall of a said inner pipe; and motorized displacement means for moving said probe in translation along said axial direction and in rotation about the axis of said pipe, enabling it to travel around the circumference of the inside surface of said inner pipe; and automatic electronic control means for said probe displacement means; and electronic means for analyzing and controlling the signals from said probe and connected to said probe.

According to the invention, the device comprises:

a structure suitable for fitting to the end of said inner pipe or of said junction forging with the help of fastener means;

a said structure having a central guide cavity in which a shaft is axially mounted and is suitable for being driven in axial translation inside said inner pipe, preferably with the help of jacks or an electric motor;

said shaft being suitable for being driven in rotation about its axis, preferably with the help of an electric motor, and including at its end a transverse arm extending radially relative to the axis of said inner pipe and preferably suitable for being driven in radial translation, and being suitable for being driven in rotation by rotating said shaft; and said probe being mounted at the end of said arm, preferably via a hinge or ball joint.

The present invention also provides a method of coupling an inner pipe 2 with a coaxial outer pipe 3 in an assembly of two coaxial pipes, the method being characterized by:

welding the end of said outer pipe on the surface of said inner pipe; and inspecting said weld by a method of the invention with the help of a device of the invention.

The present invention also provides a method of connecting together two unit elements of a set of two coaxial pipes each comprising an inner pipe 2 and an outer pipe 3, the method being characterized by:

assembling a junction forging to the ends of said internal and outer pipes of each unit element of a set of two pipes by welding said forging to said ends of the internal and outer pipes; and inspecting the weld between said forging and the end of the inner pipe by a method of the invention with the help of a device of the invention.

BRIEF DESCRIPTION OF THE DRAWINGS

Other characteristics and advantages of the present invention appear in the light of the following detailed description given with reference to the following figures, in which.

DETAILED DESCRIPTION OF THE PRESENTLY PREFERRED EMBODIMENTS

Figure 1:
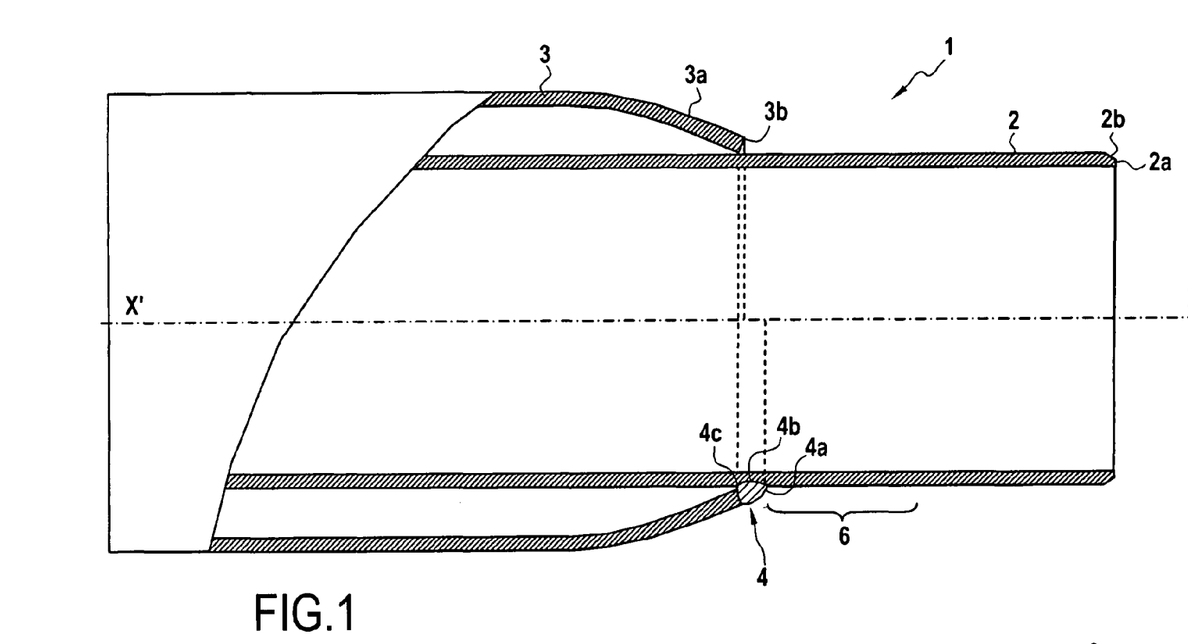
FIG. 1 is a side view in section of a PIP type pipe 1 made up of an inner pipe 2 and an outer casing 3 having its end 3a, 3b crooked and then welded at 4 onto an inner pipe 2.

FIG. 1 is a side view in section of a PIP 1 constituted by an inner pipe 2 assembled by welding 4 to an outer casing 3, the casing having previously been crooked at 3a so that its inside diameter corresponds substantially to the outside diameter of the inner pipe and as a result comes substantially into contact with said inner pipe. Because of the variations in the mechanical characteristics of the outer casing at the crooked end 3a, the distance to the inner pipe is generally not uniform all around the periphery and can vary depending on circumstances over a range of 0 to 3 millimeters (mm), or indeed over a range of 0 to 5 mm. For clarity in explanation, the crooked outer casing is shown in the top of the figure after crooking and before welding, and in the bottom of the figure after final welding.

An ultrasound test may be performed in conventional manner manually by an operator using a conventional angular probe that the operator moves axially from front to back over the zone 6 on the outside of the string, successively sweeping the entire periphery of said pipe in said zone 6. As scanning progresses, the information obtained is used in a manner known to the person skilled in the art, and possible defects if any are shown up. In this way, only the front tip 4a of the weld and the under face 4b can be inspected reliably. In contrast, the root 4c of the weld, i.e. the first welding pass, is in an opposite position towards the inside of the outer casing of the PIP, thus preventing any access thereto for inspection by conventional ultrasound means. Unfortunately, this first welding pass often determines the overall quality of the weld, since it is during this difficult stage that crack initiation sites or occlusions can occur that run the risk of propagating through the weld, generally leading rapidly to destruction of the assembly. Nevertheless, it is still possible to inspect the weld in part by proceeding in conventional manner from the outer casing over the crooked portion 3a, with the exception of the root of said weld, for which the acoustic echo of its edge cannot be distinguished from an unwanted welding defect, such as a crack initiation site.

Figure 1A:
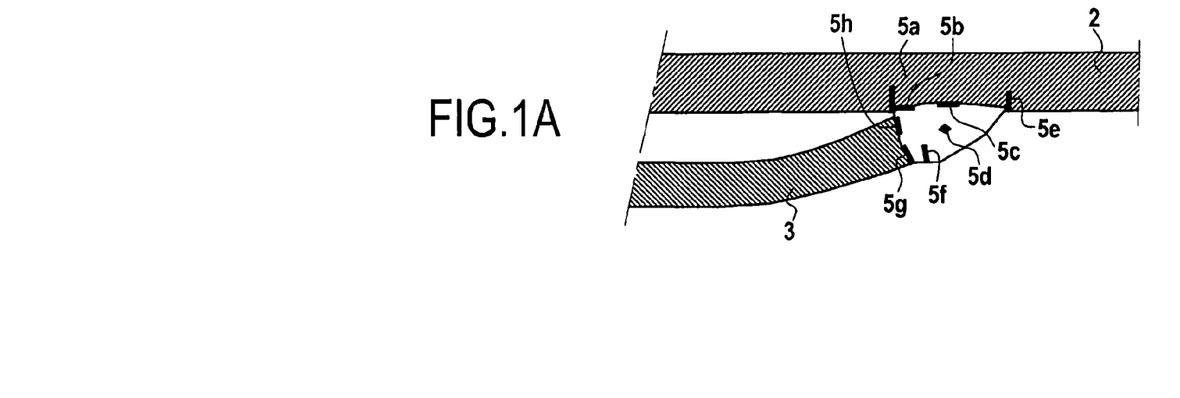
FIG. 1A shows various types of faults 5a-5h to be searched for within the weld, and in its immediate surroundings.

In FIG. 1A, there can be seen in section the various unwanted defects that it is desired to reveal so that they can be subsequently be repaired. The most critical defects are crack initiation sites 5a and 5b that are respectively radial and axial, followed by crack initiation sites 5c that are tangential to the inner pipe 1 in the root of the weld, i.e. the portion that is directly in contact with said inner pipe or interface, and finally cavities 5d located within the weld. The crack initiation sites 5a-5b are created at the very beginning of welding and they are conditioned by numerous factors, of which the following are mentioned: clearance existing between the outer casing and the inner pipe, which clearance is generally not regular around the periphery and lies in a range of 0 to 3 mm, or even 0 to 5 mm; the quality and the cleanness of the end face of the outer casing; and the effectiveness with which the stage of striking the electric arc for welding is carried out, and also the stability of the welding bath during the initial turns.

The other defects 5e to 5h are created throughout said welding process and are generally due to instability of the electric arc or the welding bath. The crack initiation sites 5e, 5f, 5g, and 5h are situated respectively at the external tip of the weld at the interface between the weld and said pipe 5e, close to the outer casing 5f, and at the interface between said weld and the branch of said outer casing 5g-5h. These defects 5e, 5f, 5g, and 5h can easily be revealed from the outside using conventional means operated manually by the inspector, said means being ultrasound for 5e-5g-5h, and sweating or inspection with magnetic particles for 5e-5f-5g.

Figure 2:
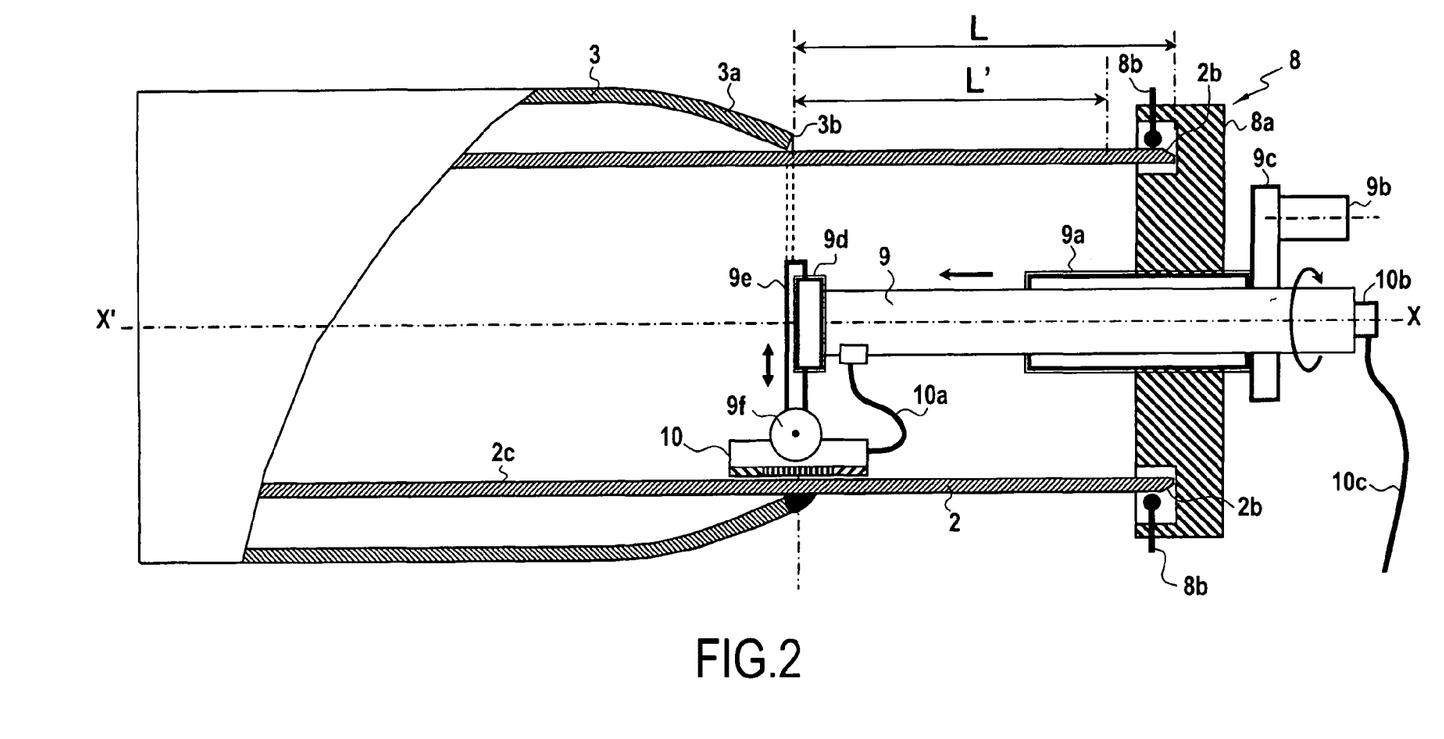
FIG. 2 is a side view in section showing the device 8 of the invention for automatically inspecting welding by ultrasound from inside the inner pipe of a FIG. 1 PIP pipe.

FIG. 2 is a side view in section of a PIP 1 having installed at the end thereof a robot of the invention for inspecting welding by ultrasound, making it possible automatically to inspect the weld zone 4 in order to detect mainly defects of types 5a-5b-5c-5d, and possibly defects of the other types mentioned above. For this purpose, the device 8 of the invention is constituted by a structure 8a suitable for fitting to the end of the inner pipe that has previously been machined in its end face 2a, and possibly on its chamfer 2b, in order to enable it to be subsequently connected by welding to a second string or to a junction forging, which connection is performed on site on board a laying ship fitted with a J-lay tower. The structure 8a is centered relative to the axis XX of the PIP and is held in place by adjustable clamping means 8b. A shaft 9, which is movable in translation along the axis XX in a guide barrel 9a that is secured to the structure 8a and which passes axially therethrough, is itself moved in translation along said axis XX by an actuator (not shown) that may be constituted, for example, by a jack or an electric motor, and that is preferably servo-controlled by a computer. In addition, said shaft 9 is movable in rotation about the same axis XX within the guide barrel 9a. Said rotation of the shaft 9a is driven via a transmission element 9c by an electric motor 9b that is preferably servo-controlled by said computer. At the front of the shaft 9, a guide support 9d secured to said shaft holds a transverse arm 9e and guides it perpendicularly to the inside wall 2c of the inner pipe 2, said arm 9e supporting an ultrasound probe 10 secured thereto by means of a hinge 9f of axis perpendicular to the plane of the Figure. Said ultrasound probe is held in intimate contact with the inside wall 2c of the inner pipe 2, preferably with a constant bearing force, by means of an actuator that is not shown, e.g. a pneumatic jack. A film of water for providing coupling between the ultrasound probe and the metal inside wall is maintained in known manner throughout the duration of the inspection cycle. For clarity in the drawings, the probe 10 is always shown in the figures as being at a short distance from the wall 2c of the pipe 2, however in fact it is practically in direct contact with said wall via the coupling film which is generally a film of water. An electric cable 10a conveys excitation and reception currents to and from the ultrasound transducers between the probe (passing via the inside of the shaft 9 to a rotary joint 10b preferably situated behind the main shaft 9 and on its axis) and various electronic monitoring and control devices (not shown) by means of an electric cable 10c.

Figure 2A:
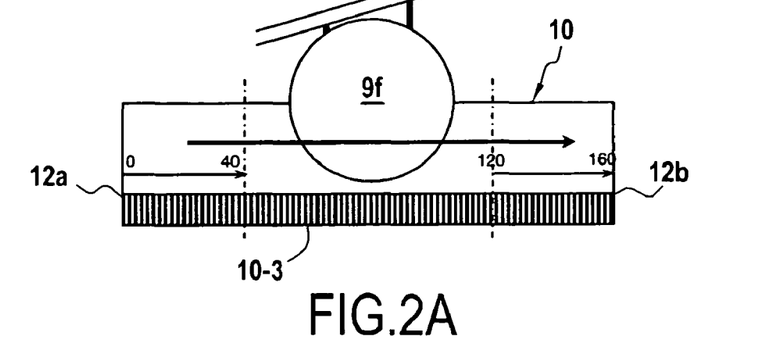
FIGS. 2A-2B are side views in section showing a probe 10 for automatically inspecting welding by ultrasound, the probe being of the phased-array multibeam type, having a single zone (FIG. 2A) or a plurality of zones (FIG. 2B) each containing a series of emitters that emit in different directions.

FIG. 2A is a side view in section of an ultrasound probe 10 having an array of piezoelectric probes, i.e. of emitter-receivers, with a particular method of operation thereof being explained below. This type of probe is known as a phased array, i.e. it is a multi-element probe with sequential triggering, made up of 16 to 1024 piezoelectric emitter-receivers disposed in a line and capable of emitting and receiving waves perpendicularly to the bottom face of said probe. Each of the groups of piezoelectric elements is triggered in sequence at a regular interval after the preceding group, starting from the first element 12a situated to the left of the probe and continuing to the last element 12b situated to the right of the probe, as shown in said FIG. 2A. The emitters are configured as emitters and as receivers and the information received is transmitted to the electronic devices for processing the signal so as to display in real time the positions of the looked-for defects.

Figure 2B:
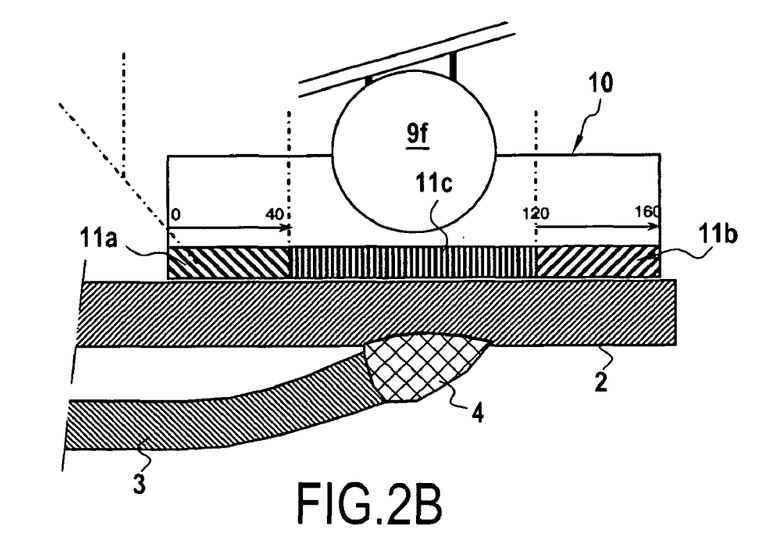
Figure 2C:
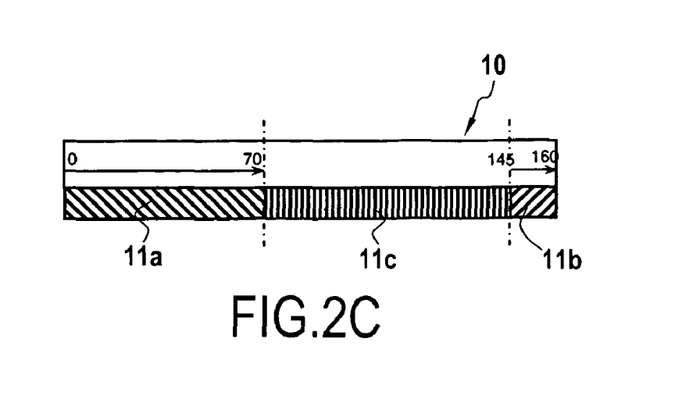
FIG. 2C shows a variant of FIG. 2B.

In FIG. 2A, all of the beams are shown as being perpendicular to the probe, which corresponds to a regular interval between the triggering of emitter N and of emitter N+1, in the absence of any interference between said emitters. The feature of this type of probe is that the controlling electronics is capable of delivering trigger signals at intervals that can be varied and that are extremely accurate, so that triggering emitter N creates a disturbance on sound beam N−1, N−2, etc., and also on future beams N+1, N+2, etc., thereby creating, by destruction of the emitted signals, beams that are no longer perpendicular, but that are at an angle α relative to the plane of the bottom face of the probe. The computer management with the control system thus serves to direct the beams from each of the emitters. In the present invention, as shown in FIG. 2B, a first zone comprising a first series 11a of emitters referenced N−0 to N−40 is configured with an angle α=45° directed to the right, and is followed by a second zone of a series 11c of emitters referenced N−41 to N−120 in the middle portion that are configured perpendicularly, and finally followed by a third zone of a series of emitters referenced N−121 to N−160 that are configured to have an angle α=−45° directed to the left. Thus, in a single scan sequence, all of the information needed for revealing defects in the plane under inspection is picked up, firstly from the root zone 4c of the weld, by the first series of emitter-receivers, and then from the weld zone proper 4b, by the second series of emitter-receivers, and finally from the tip zone 4a of the weld, by means of the third series of emitter-receivers. Unlike the manual displacement of a conventional probe as performed by an operator who is required to scan axially from front to rear along the direction XX' over the weld zone for inspection, the probe remains stationary, and the axial scanning is performed electronically and entirely automatically by the control system operating said probe. In addition, it is possible to modify the various zones as shown in FIG. 2C where the three ranges as described above are reorganized with the values N−0 to N−70, N−70 to N−145, and N−145 to N−160. This advantageously enables the accuracy in the first and third zones at the angle α to be improved considerably by configuring a mean angle in each of them, e.g. α=45° with the angle varying from α=30° at emitter N−0 to α=50° at emitter N−40, thereby enabling the beam to be focused and leading to better location of the looked-for defects.

Such a phased-array ultrasound inspection system that is configurable on demand as explained above is available under the name Omniscan from the supplier R/D Tech—Canada.

Once the multi-element probe 10 has been correctly configured, the device of the invention is installed as shown in detail in FIG. 2, and the position of said probe is adjusted very accurately relative to the zone for inspection. To this end, before welding is performed, the distance L from the edge 3b at the end of the outer casing, to the front face at the end of the inner pipe, is measured accurately, and the weld of the shaft 9 is then merely adjusted so that the multi-element probe 10 is positioned with great accuracy relative to the weld 4. The automatic cycle of circumferential rotation is then initiated, starting from an accurately identified starting position, e.g. the bottom tangent of the inner pipe as shown in all of the figures. Since the shaft 9 is in a stationary position in translation corresponding to the zero reference point, a first scan from N–0 to N–160 is performed by the control device, and then the shaft 9, and thus the probe, is pivoted about the axis XX, e.g. clockwise, using the actuator 9b under the control of said control system, through an angle increment, e.g. through 0.1°, corresponding to a circular arc of a size greater than the minimum size of defects that it is desired to be able to detect in the weld, given the diameter of the pipe, specifically 0.26 mm for an inner pipe having an outside diameter of 300 mm. The probe then faces a new circumferential sector on a radial plane containing the axis XX' and offset through 0.1°, and a new scan from N–0 to N–160 is carried out in this sector, and so on until a complete revolution has been performed around the circumference, representing 3600 cycles with said increment of 0.1°.

All of the information is processed in a manner known to the person skilled in the art within the computer system, and the results are then printed in synthesized form, generally using false colors so as to show up more clearly the defects and their types, in a form that can be used easily and directly.

When the front face 3b at the end of the inner pipe is a raw cut and therefore irregular, or when the plane of its section is not perpendicular to its axis, said face cannot be used as a reference for accurately positioning the device 8. Under such circumstances, it is then advantageous, prior to making the weld 4, to mark a circle at a distance L' from the edge 3b so as to create a circular reference mark at said distance L' from said edge. It then suffices to place the structure 8a at a known distance from said mark for the probe 10 to be in the desired position relative to the weld 4 for inspection. When the edge 3b does not lie in a plane perpendicular to the axis XX', the mark will suffer from the same deformation; in which case the structure 8a should be positioned in a mean position relative to said mark. Marking is described as being relative to the top edge 3b, but the accuracy of the mark made is advantageously improved by performing said operation relative to the bottom edge of the crooked end, said edge being substantially in contact with the inner pipe.

Figure 3:
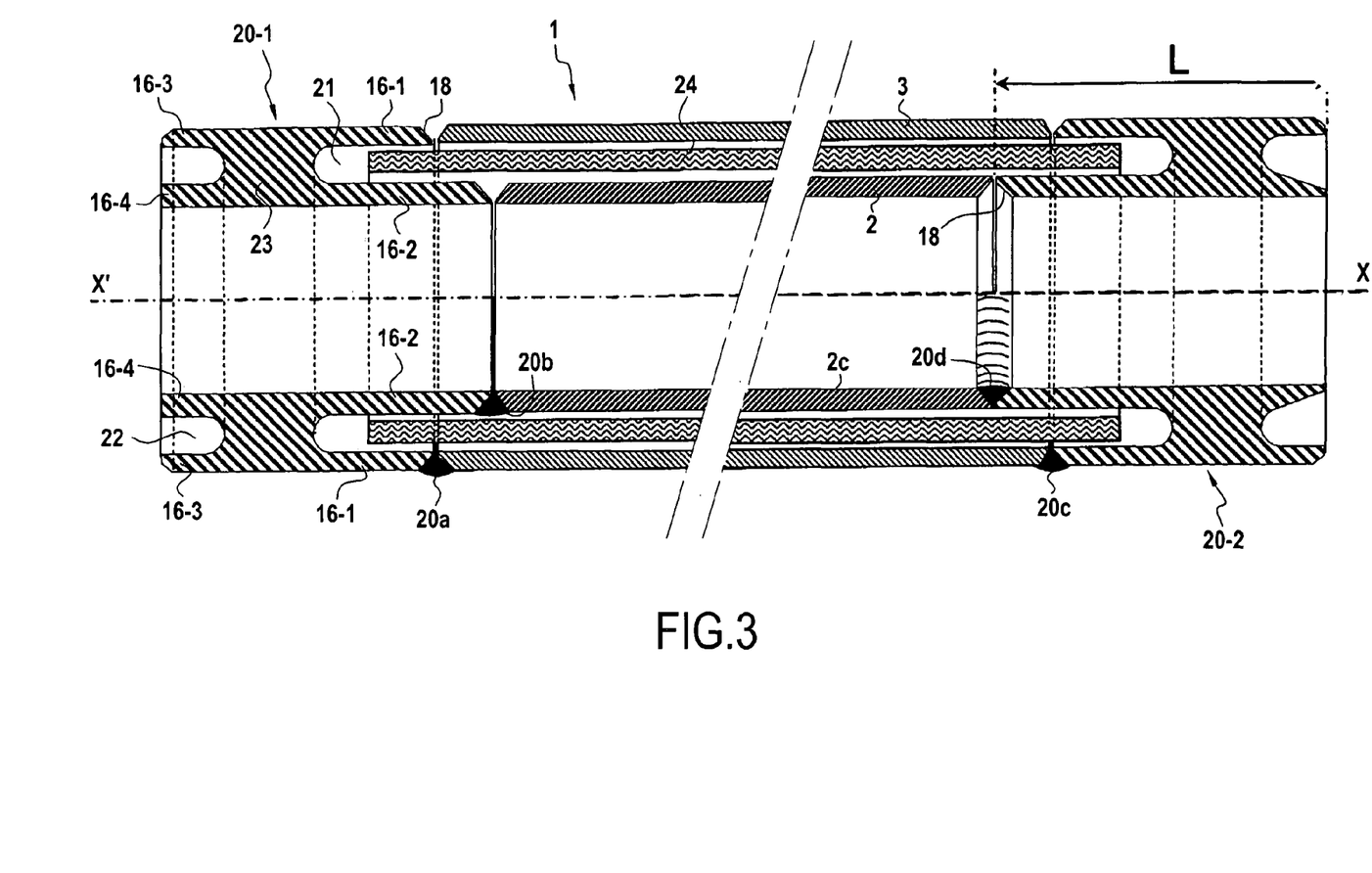
FIG. 3 is a side view in section of a PIP pipe string 1 in which the inner pipe 2 and the outer casing 3 are assembled together by being welded 20a-20d to a circularly-symmetric forged junction part 20.

FIG. 3 shows two ends of a string 1 made up of an outer casing 3 and an inner pipe 2 connected in known manner at each of their ends to a junction forging 20, on the left of the figure via welds 20a and 20b respectively with the outer and inner pipes that are made from the outside, whereas on the right in the same Figure, the weld 20c is made from the outside and the weld 20d is made from the inside of the inner pipe 2.

Figure 4:
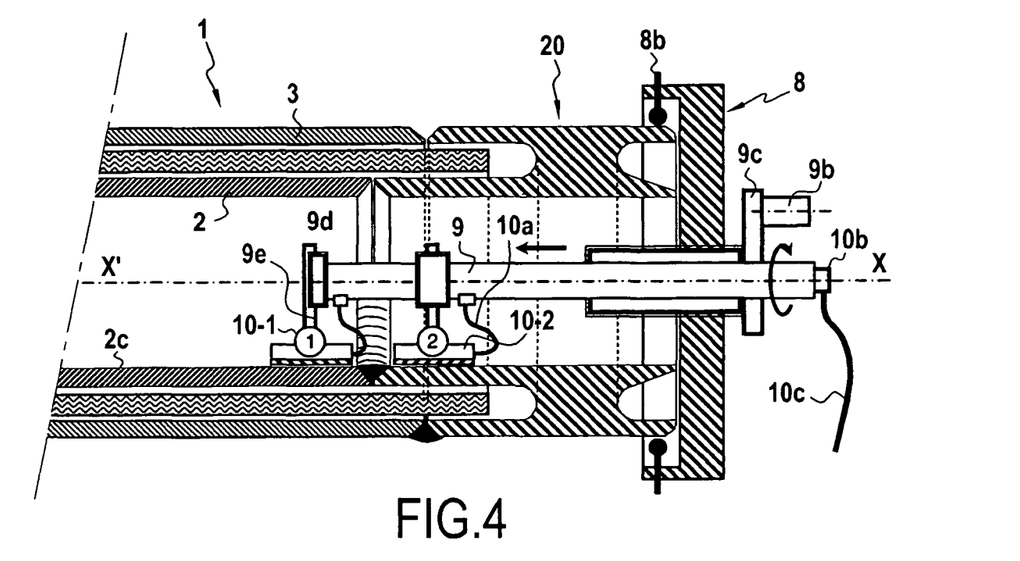
FIG. 4 is a side view in section showing the device 8 of the invention for automatically inspecting welding by ultrasound, from inside the inner pipe of a FIG. 3 PIP pipe.

The internal welds between the ends of the inner pipe and the forging 20b and 20d are advantageously inspected using the same inspection device 8, but it must then be fitted with two probes 10-1 and 10-2 as shown in detail in FIG. 4. In this configuration, said beads of welding pass right through the wall of the inner pipe, so the inside surface 2c of said inner pipe 2 is not uniform and presents extra thickness that is often quite variable and that is located all around its circumference.

Since the forging 20 is precision-machined, the length L is known and it is then very simple to install the device 8 at the end of said forging and to adjust the position of the arm 9 so that all of the probes 10-1 and 10-2 are correctly positioned on either side of the bead of welding for inspection. The mode of operation is identical to that described with reference to FIGS. 2-2A-2B-2C, however in this configuration, as shown in FIG. 4A, the probe 10-1 is configured with an angle that is constant or that varies slightly, e.g. α=45°, whereas the probe 10-2 is configured with an angle that is symmetrical and constant or slightly variable, e.g. α=–45°.

Figure 4A:
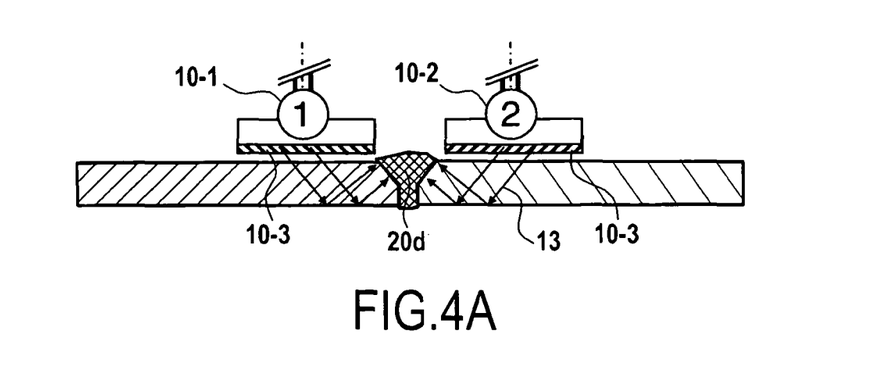
FIG. 4A shows the operation of the two independent probes 10-1, 10-2 of FIG. 4.

To understand the ultrasound inspection process, FIG. 4A also shows the paths followed by the emitted soundwaves 13. After being reflected on a defect, the return wave follows a reverse path with time delays due to the distance traveled. Recording these time delays and also the amplitude of the signal makes it possible by processing the signal to produce a graphical representation of the defects, in type, size, and position.

A conventional ultrasound probe is constituted by a piezoelectric emitter of ceramic material placed against the outside wall of the pipe at the weld, that emits over a short period a signal in the form of ultrasound waves, after which the signal is coupled to the mass of steel via a coupling medium (generally water), and then reverberates on the opposite face of the wall of the inner pipe and also on any defect which is then considered as being an obstacle. The return signal is received by a sensor, generally said emitter that also acts as a receiver, and then the signal is delivered to electronic processor means which process the signal and then display information, generally in directly exploitable form on a screen or printed on paper.

In FIG. 3, said junction forging 20-1, 20-2 is defined as follows:
  in a radial direction relative to a longitudinal axis XX' of revolution of said forging, it is defined by a cylindrical inside wall having substantially the same diameter as the main portion of said inner pipe 2, and by a cylindrical outside wall of diameter substantially equal to the outside diameter of the main portion of said outer casing 3; and
  in the longitudinal axial direction XX':
    on the side of said junction forging that is to be welded to the ends of said outer and inner pipes of a said element of a set of at least two coaxial pipes, said outside wall and inside wall of said junction forging form in longitudinal section respective outer and inner first branches 16-1 and 16-2 that are of substantially the same thicknesses as said outer and inner pipes 3 and 2 with which they are to be assembled, said outer and inner first branches 16-1, 16-2 defining a first annular cavity 21; and
    on the opposite side of said junction forging that is to be assembled with another said junction forging, itself welded to the end of another assembly of two coaxial pipes, said outside and inside walls form in longitudinal section respective external and internal second branches 16-3 and 16-4 that define a second annular cavity 22; and
    the bottoms of said first and second cavities 21 and 22 are spaced apart in said longitudinal direction XX' so as to define a solid zone 23 of said junction forging in which said outer and inner walls form the outside and inside faces of a given cylindrical wall.

As shown in FIG. 3, the first annular cavity 21 is open over the annular space and can receive the insulation material 24 so as to continue the insulation of the pipe as far as possible.

After assembling and connecting together two unit lengths of PIP fitted with junction forgings of the invention, the second annular cavity 22 of a first junction forging at the downstream end of a first length of PIP is open over a second annular cavity of a second junction forging 20-1 at the upstream end of a second length of PIP, thus forming a chamber that is made by welding together the ends of the second outer branches 16-3. However this chamber is not sealed since the ends of the inner second branches 16-4 of the two junction forgings 20-1, 20-2 are not welded together, the faces of said branches merely being in contact with each other.

The free ends of said outer and inner first branches 16-1 and 16-2 present chamfered shapes 8 making it possible in known manner to perform a so-called "full penetration" first welding pass followed by complete filling of the chamfer on the left (FIG. 3), the chamfers 18 facing towards the outside and thus being suitable for being welded from outside said outer and inner pipes 3 and 2. On the right, the chamfers 18 face outwards at the end of said outer first branch and inwards at the end of said inner first branch, making them suitable for being welded respectively from outside said assembly for said outer first branches and from inside inner pipe for said inner first branches.

In FIG. 3, the free ends of said outer second branch 16-1 present the shape of a chamfer 18 facing towards the outside of a first junction forging 20-1 making them suitable for being welded from the outside to the free end of another said outer second branch of another junction forging 20-2 with which it is to be assembled, said other junction forging itself being at the end of a second unit comprising an assembly of two coaxial pipes.

In the junction forging 6*a*, the end of said inner first branch 16-2 on the side of said junction forging that is suitable for being assembled directly to a said element of a set of coaxial pipes, projects in the axial longitudinal direction XX' relative to the end of a said outer first branch 16-1 so that the junction forging can be assembled by welding to a said set of coaxial pipes in which the end of said outer pipe projects relative to the end of said inner pipe.

The junction forgings 20-1 and 20-2 present an outside diameter and a wall thickness that are substantially equal to, and that are preferably exactly equal to, the outside diameter and the thickness of the main portion of the outer casing. Thus, the pipe presents a substantially constant second moment of area over its entire length, thus avoiding concentrating stresses at the connections between two unit lengths of PIP, and considerably improving the bending and fatigue behavior of the pipe, thereby enabling it to remain intact over the entire lifetime of installations that can reach or exceed 30 years, particularly when used to provide bottom-to-surface connections that are subjected to the effects of swell and current.

The invention claimed is:

1. A method of inspecting a substantially circular circumferential weld for connecting an inner pipe to a coaxial outer pipe, either directly or else via a junction forging, inspection being performed by an ultrasound probe, the method comprising the steps of:
   using a robotic ultrasound probe comprising a plurality of multibeam piezoelectric emitter-receivers;
   a) positioning at least one said ultrasound probe inside said inner pipe, at a given position in the longitudinal axial direction of said inner pipe against the inside surface of the wall of said inner pipe, said given position facing or being close to said weld, so that the ultrasound beams from the various emitters in the axial plane of said inner pipe perpendicular to the plane of the bottom faces of said emitters cover at least the entire width of the weld in said longitudinal axial direction;
   b) causing the various ultrasound beams of the various emitters of said probe to scan while the probe is positioned in said given position;
   c) moving said probe in rotation about the longitudinal axis of said pipe through a given angle of rotation, and then
   d) repeating steps b) and c) until the entire circumference of said weld has been inspected;
   wherein the ultrasound beams from the various emitters are sent in said axial plane of the inner pipe in a plurality of different angles of inclination having different values relative to the plane of said bottom faces of said emitters so that in a single sequence of scanning the various beams, the various zones of said weld are inspected across its width; and
   wherein said emitters are arranged in three contiguous zones in the longitudinal axial direction, comprising:
   a first zone in which the emitters are offset in said longitudinal axial direction relative to said weld, and emit beams at a first angle of inclination towards said weld;
   a central second zone in register with at least the middle portion of the width of said weld, and in which said emitters emit beams at a second angle of inclination substantially perpendicular to the plane of said bottom faces of said emitters; and
   a third zone at the end of said central second zone opposite from the end at which said first zone is located, and likewise offset in said longitudinal axial direction relative to said weld and emitting beams at a third angle of inclination opposite to said first angle of inclination towards said weld.

2. The method according to claim 1, wherein:
   the various beams of said first zone extend in parallel to each other and said first angle of inclination lies in the range 30° to 60°; and
   the various beams of said third zone extend parallel to each other.

3. The method according to claim 1, wherein said first angle of inclination comprises a plurality of angles, the plurality of angles of the various beams of said first zone increasing from 30° to 60° from the emitter that is furthest away from the center of said weld to the emitter that is closest thereto.

4. The method according to claim 1 wherein each said zone of emitters comprises 16 to 1024 piezoelectric elements.

5. The method according to claim 1 wherein said weld is made from outside said inner pipe.

6. The method according to claim 1 wherein said weld is made from the inside of said inner pipe.

7. The method according to claim 6 wherein said weld connects the end of said inner pipe to the end of a junction forging.

8. The method according to claim 6 wherein said weld presents extra thickness relative to the inside surface of the wall of said inner pipe, and two of said ultrasound probes are placed against said inside surface on either side of said weld, each of said probes comprising a plurality of emitters emitting beams towards said weld.

9. The method according to claim 1, wherein said given angle of rotation is less than 1°.

10. The method according to claim 1, wherein said given angle of rotation corresponds to an arc of length that is no greater than the size of the weld defects that are to be detected.

11. The method according to claim 1, wherein the ultrasound beams from the various emitters are sent in said axial plane of the inner pipe in a plurality of different angles of inclination having different values relative to the plane of said bottom faces of said emitters so that in a single sequence of scanning the various beams, the various zones of said weld are inspected across its width, from the external tip to the root of said weld at the interface with said inner pipe.

12. A method of inspecting a substantially circular circumferential weld for connecting an inner pipe to a coaxial outer pipe, either directly or else via a junction forging, inspection being performed by an ultrasound probe, the method comprising the steps of:

using a robotic ultrasound probe comprising a plurality of multibeam piezoelectric emitter-receivers;

a) positioning at least one said ultrasound probe inside said inner pipe, at a given position in the longitudinal axial direction of said inner pipe against the inside surface of the wall of said inner pipe, said given position facing or being close to said weld, so that the ultrasound beams from the various emitters in the axial plane of said inner pipe perpendicular to the plane of the bottom faces of said emitters cover at least the entire width of the weld in said longitudinal axial direction from the external tip to the root of said weld at the interface with said inner pipe;

b) causing the various ultrasound beams of the various emitters of said probe to scan while the probe is positioned in said given position;

c) moving said probe in rotation about the longitudinal axis of said pipe through a given angle of rotation; and then d) repeating steps b) and c) until the entire circumference of said weld has been inspected;

wherein said weld is on the outside of said pipe; and wherein said weld connects the end of said outer pipe to the outside surface of the wall of said inner pipe, the end of said outer pipe being set back from the end of said inner pipe.

13. The method according to claim 12 wherein said weld is made from the inside of said inner pipe, and said weld connects the end of said inner pipe to the end of a junction forging.

14. A device for inspecting a circumferential weld and usable to inspect a substantially circular circumferential weld for connecting an inner pipe to a coaxial outer pipe either directly or else via a junction forging, the device comprising:

at least one robotic ultrasound probe comprising a plurality of multibeam piezoelectric emitter-receivers;

mechanical support means for supporting said probe in position against the inside surface of the wall of said inner pipe;

motorized displacement means for moving said probe in translation along the longitudinal axial direction of said inner pipe and in rotation about the longitudinal axis of said inner pipe, enabling it to travel around the circumference of the inside surface of said inner pipe;

automatic electronic control means for said probe displacement means; and electronic means for analyzing and controlling the signals from said probe and connected to said probe;

the device further comprises:

a structure suitable for fitting, with the help of fastener means, to the end of said inner pipe or to the end of said junction forging;

said structure having a central guide cavity in which a shaft is axially mounted and is suitable for being driven in axial translation inside said inner pipe;

said shaft being suitable for being driven in rotation about its longitudinal axis, and including at its end a transverse arm extending radially relative to the longitudinal axis of said inner pipe and being suitable for being driven in rotation by rotating said shaft; and said probe being mounted at the end of said arm.

15. A method of coupling an inner pipe with a coaxial outer pipe in an assembly of two coaxial pipes, the method comprising the steps of:

welding the end of said outer pipe on the surface of said inner pipe so as to form a circular circumferential weld; and inspecting said weld with a device comprising:

at least one robotic ultrasound probe comprising a plurality of multibeam piezoelectric emitter-receivers;

mechanical support means for supporting said probe in position against the inside surface of the wall of said inner pipe;

motorized displacement means for moving said probe in translation along said longitudinal axial direction of said inner pipe and in rotation about the longitudinal axis of said inner pipe, enabling it to travel around the circumference of the inside surface of said inner pipe;

automatic electronic control means for said probe displacement means; and electronic means for analyzing and controlling the signals from said probe and connected to said probe;

the device further comprises:

a structure suitable for fitting, with the help of fastener means, to the end of said inner pipe or to the end of said junction forging;

said structure having a central guide cavity in which a shaft is axially mounted and is suitable for being driven in axial translation inside said inner pipe, with the help of jacks or an electric motor;

said shaft being suitable for being driven in rotation about its longitudinal axis, with the help of an electric motor, and including at its end a transverse arm extending radially relative to the longitudinal axis of said inner pipe and suitable for being driven in radial translation, and being suitable for being driven in rotation by rotating said shaft; and said probe being mounted at the end of said arm, via a hinge or ball joint.

16. The method of claim 15, wherein said weld is a substantially circular circumferential weld for connecting an inner pipe to a coaxial outer pipe, either directly or else via a junction forging, inspection being performed by the at least one ultrasound probe, the method further comprising the steps of:

a) positioning said at least one said ultrasound probe inside said inner pipe, at a given position in the longitudinal axial direction of said inner pipe against the inside surface of the wall of said inner pipe, said given position facing or being close to said weld, so that the ultrasound beams from the various emitters in the axial plane of said inner pipe perpendicular to the plane of the bottom faces of said emitters cover at least the entire width of the weld in said longitudinal axial direction;

b) causing the various ultrasound beams of the various emitters of said probe to scan while the probe is positioned in said given position;

c) moving said probe in rotation about the longitudinal axis of said pipe through a given angle of rotation, and then d) repeating steps b) and c) until the entire circumference of said weld has been inspected.

17. The method according to claim 15 wherein said weld is made from outside said inner pipe, and said weld connects the end of said outer pipe to the outside surface of the wall of said inner pipe, the end of said outer pipe being set back from the end of said inner pipe.

18. The method according to claim 15 wherein said weld is made from the inside of said inner pipe, and said weld connects the end of said inner pipe to the end of a junction forging.

19. A method of connecting together two unit elements of a set of two coaxial pipes each comprising an inner pipe and an outer pipe comprising the steps of:
- assembling a junction forging to the ends of said inner and outer pipes of each unit element of a set of two pipes by welding said forging to said ends of the inner and outer pipes; and
- inspecting the circular circumferential weld between said forging and the end of the inner pipe by using a device comprising:
  - at least one robotic ultrasound probe comprising a plurality of multibeam piezoelectric emitter-receivers;
  - mechanical support means for supporting said probe in position against the inside surface of the wall of said inner pipe;
  - motorized displacement means for moving said probe in translation along the longitudinal axial direction of said inner pipe and in rotation about the longitudinal axis of said inner pipe, enabling said probe to travel around the circumference of the inside surface of said inner pipe;
  - automatic electronic control means for said probe displacement means; and
  - electronic means for analyzing and controlling the signals from said probe and connected to said probe;
- the device further comprises:
  - a structure suitable for fitting to the end of said inner pipe or of said junction forging with the help of fastener means;
  - said structure having a central guide cavity in which a shaft is axially mounted and is suitable for being driven in longitudinal axial translation inside said inner pipe, with the help of jacks or an electric motor;
  - said shaft being suitable for being driven in rotation about its longitudinal axis, with the help of an electric motor, and including at its end a transverse arm extending radially relative to the longitudinal axis of said inner pipe and suitable for being driven in radial translation, and being suitable for being driven in rotation by rotating said shaft; and
  - said probe being mounted at the end of said arm, via a hinge or ball joint.

* * * * *